(12) United States Patent
Brown et al.

(10) Patent No.: US 12,239,749 B2
(45) Date of Patent: Mar. 4, 2025

(54) THERMAL DISINFECTING TOOL

(71) Applicant: The Boeing Company, Chicago, IL (US)

(72) Inventors: Myles E Brown, Everett, WA (US); Colin Hart, Everett, WA (US); Trevor M Laib, Woodinville, WA (US)

(73) Assignee: The Boeing Company, Arlington, VA (US)

( * ) Notice: Subject to any disclaimer, the term of this patent is extended or adjusted under 35 U.S.C. 154(b) by 710 days.

(21) Appl. No.: 17/501,100

(22) Filed: Oct. 14, 2021

(65) Prior Publication Data
US 2022/0118127 A1    Apr. 21, 2022

Related U.S. Application Data

(60) Provisional application No. 63/093,646, filed on Oct. 19, 2020.

(51) Int. Cl.
| | | |
|---|---|---|
| *A61L 2/06* | (2006.01) | |
| *A61L 2/24* | (2006.01) | |
| *A61L 2/28* | (2006.01) | |
| *B64D 13/06* | (2006.01) | |

(Continued)

(52) U.S. Cl.
CPC .............. *A61L 2/06* (2013.01); *A61L 2/24* (2013.01); *A61L 2/28* (2013.01); *B64D 13/08* (2013.01); *B64F 5/30* (2017.01); *A61L 2202/25* (2013.01); *B64D 2013/0603* (2013.01)

(58) Field of Classification Search
CPC ...... A61L 2/06; A61L 2/24; A61L 2/28; B64F 5/30; B64D 13/08
See application file for complete search history.

(56) References Cited

U.S. PATENT DOCUMENTS

| | | |
|---|---|---|
| 2020/0075972 A1 | 3/2020 | Jorgenson et al. |
| 2022/0054673 A1 | 2/2022 | Wiemeersch et al. |
| 2022/0055449 A1 | 2/2022 | Wiemeersch et al. |

FOREIGN PATENT DOCUMENTS

| | | |
|---|---|---|
| EP | 3922272 A1 | 12/2021 |
| KR | 20130031730 A | 3/2013 |
| WO | 2022000075 A1 | 1/2022 |

OTHER PUBLICATIONS

Boudette, Neal E. "To Disinfect a Police Car in a Pandemic, Software Cranks Up the Heat," The New York Times, May 30, 2020, pp. 1-4.

(Continued)

*Primary Examiner* — Sean E Conley
(74) *Attorney, Agent, or Firm* — Kolitch Romano Dascenzo Gates LLC

(57) ABSTRACT

A thermal disinfecting tool for disinfecting surfaces bounding or located within a fixed volume of air is disclosed and includes a housing and a heater. The housing defines one or more inlets and one or more outlets. Air is drawn from the fixed volume of air through the one or more inlets and exits the housing through the one or more outlets. The heater is disposed within the housing downstream of the one or more inlets and upstream of the one or more outlets. The thermal disinfecting tool also includes one or more processors in electronic communication with the heater and a memory coupled to the one or more processors, where the memory stores a time to inactivation plot for a specific pathogen that indicates a deactivation time for the specific pathogen over a range of temperatures.

20 Claims, 8 Drawing Sheets

(51) Int. Cl.
*B64D 13/08* (2006.01)
*B64F 5/30* (2017.01)

(56) References Cited

OTHER PUBLICATIONS

European Patent Office. Extended European Search Report for EP Application No. 21203251.0, mailed Mar. 18, 2022, pp. 1-5.

THERMAL DISINFECTING TOOL

CROSS-REFERENCE TO RELATED APPLICATION

This application claims priority to U.S. Provisional Application No. 63/093,646, filed Oct. 19, 2020. The contents of the application are incorporated herein by reference in its entirety.

INTRODUCTION

The present disclosure relates to a thermal disinfecting tool. More particularly, the present disclosure is directed towards a thermal disinfecting tool for disinfecting surfaces bounding or that are located inside a fixed volume of air using heat.

BACKGROUND

The flight deck of an aircraft contains various instruments and controls. Some of the instruments and controls on the flight deck may be repeatedly touched or otherwise manipulated by the pilot and copilot while operating the aircraft. In fact, the flight deck may include hundreds of touch points. As a result, the various instruments and other surfaces located in the flight deck may require disinfection between flights to inactivate pathogens such as viruses and bacteria.

Several approaches currently exist for disinfecting the instrumentation on a flight deck. For example, chemical disinfectants may be used to inactivate the pathogens that exist on the various surfaces of a flight deck. However, many components on the flight deck have not been tested for the effects of frequent or extended exposure to chemical disinfectants.

Alternatively, in another approach, ultraviolet light may be used to disinfect the various surfaces of the flight deck. For example, a portable tool such as a wand that emits ultraviolet light may be provided for disinfecting the flight deck. However, some types of wands may be bulky or heavy. As a result, some individuals may find it difficult to maneuver the wand. This issue may be further compounded when using the wand in confined areas such as a flight deck of an aircraft. Furthermore, the effectiveness of ultraviolet light disinfection depends on the line-of-sight exposure of the contaminants with respect to the ultraviolet light. Environments such as the aircraft's flight deck include obstacles or barriers that tend to block the ultraviolet light emitted by the wand, thereby reducing the effectiveness of the wand. Finally, some types of wands may require specialized training to operate.

SUMMARY

According to several aspects, a thermal disinfecting tool for disinfecting surfaces bounding or located inside a fixed volume of air is disclosed. The thermal disinfecting tool includes a housing and a heater. The housing defines one or more inlets and one or more outlets. Air enters the housing through the one or more inlets and exits the housing through the one or more outlets. The heater is configured to generate heat. The heater is disposed within the housing downstream of the one or more inlets and upstream of the one or more outlets. The thermal disinfecting tool also includes one or more processors in electronic communication with the heater and a memory coupled to the one or more processors, the memory storing a time to inactivation plot for a specific pathogen that indicates a deactivation time for the specific pathogen over a range of temperatures. The memory stores data into one or more databases and program code that, when executed by the one or more processors, causes the thermal disinfecting tool to receive a signal indicating a current inlet temperature of air entering the one or more inlets of the housing and compare the current inlet temperature of the air with a target temperature located on the time to inactivation plot stored in the memory. In response to determining the current inlet temperature is less than the target temperature, the one or more processors calculate a disinfection rate for the surfaces bounding or located within the fixed volume of air based on the time to inactivation plot for each current inlet temperature up to the target temperature, where the disinfection rate indicates a period of time required to deactivate the specific pathogen disposed on the surfaces bounding or located within the fixed volume of air at the current inlet temperature until the target temperature is reached. The one or more processors instruct the heater to generate heat for the period of time required to deactivate the specific pathogen.

In another aspect, a method for disinfecting surfaces bounding or located within a fixed volume of air by a thermal disinfecting tool is disclosed. The method includes activating, by a control module, a heater, wherein the heater is disposed within a housing of the thermal disinfecting tool. The method also includes receiving, by the control module, a signal indicating a current inlet temperature of air entering the housing. The method also includes comparing, by the control module, the current inlet temperature of the air with a target temperature located on a time to inactivation plot stored in a memory of the control module, where the time to inactivation plot is for a specific pathogen and indicates a deactivation time for the specific pathogen over a range of temperatures. In response to determining the current inlet temperature is less than the target temperature, the method includes calculating a disinfection rate for the surfaces bounding or located within the fixed volume of air based on the time to inactivation plot for each current inlet temperature up to the target temperature. The disinfection rate indicates a period of time required to deactivate the specific pathogen disposed on the surfaces bounding or located within the fixed volume of air at the current inlet temperature until the target temperature is reached. Finally, the method includes instructing the heater to generate heat for the period of time required to deactivate the specific pathogen.

The features, functions, and advantages that have been discussed may be achieved independently in various embodiments or may be combined in other embodiments further details of which can be seen with reference to the following description and drawings.

BRIEF DESCRIPTION OF THE DRAWINGS

The drawings described herein are for illustration purposes only and are not intended to limit the scope of the present disclosure in any way.

DETAILED DESCRIPTION

The present disclosure is directed towards a thermal disinfecting tool for disinfecting surfaces bounding or inside a fixed volume of air using heat. The thermal disinfecting tool includes a housing defining one or more inlets and one or more outlets. The thermal disinfecting tool also includes a control module in electronic communication with one or more inlet sensors configured to monitor a current inlet temperature of the air entering the housing, one or more outlet sensors configured to monitor a current outlet temperature of the air exiting the housing, a heater, and a fan. The control module of the thermal disinfecting tool calculates a disinfection rate for the surfaces bounding or inside the fixed volume of air based on a time to inactivation plot for a specific pathogen, where the time to inactivation plot is saved in a memory of the control module. The time to deactivation plot indicates a deactivation time for the specific pathogen over a range of temperatures. The specific pathogen is a particular virus, bacteria, or fungus. For example, in one embodiment, the time to deactivation plot may be directed towards a specific type of virus, such as a coronavirus.

During operation of the thermal disinfectant tool, the control module compares the current inlet temperature of the air with a target temperature located on the time to inactivation plot stored in the memory. In response to determining the current inlet temperature is less than the target temperature, the control module calculates the disinfection rate for the surfaces bounding or inside the fixed volume of air based on the time to inactivation plot for each current inlet temperature up to the target temperature. The control module continues to instruct the heater to generate heat for the period of time required to deactivate the specific pathogen. In an embodiment, the thermal disinfection tool generates a notification indicating the surfaces bounding or inside the fixed volume of air have been disinfected.

The following description is merely exemplary in nature and is not intended to limit the present disclosure, application, or uses.

Figure 1:
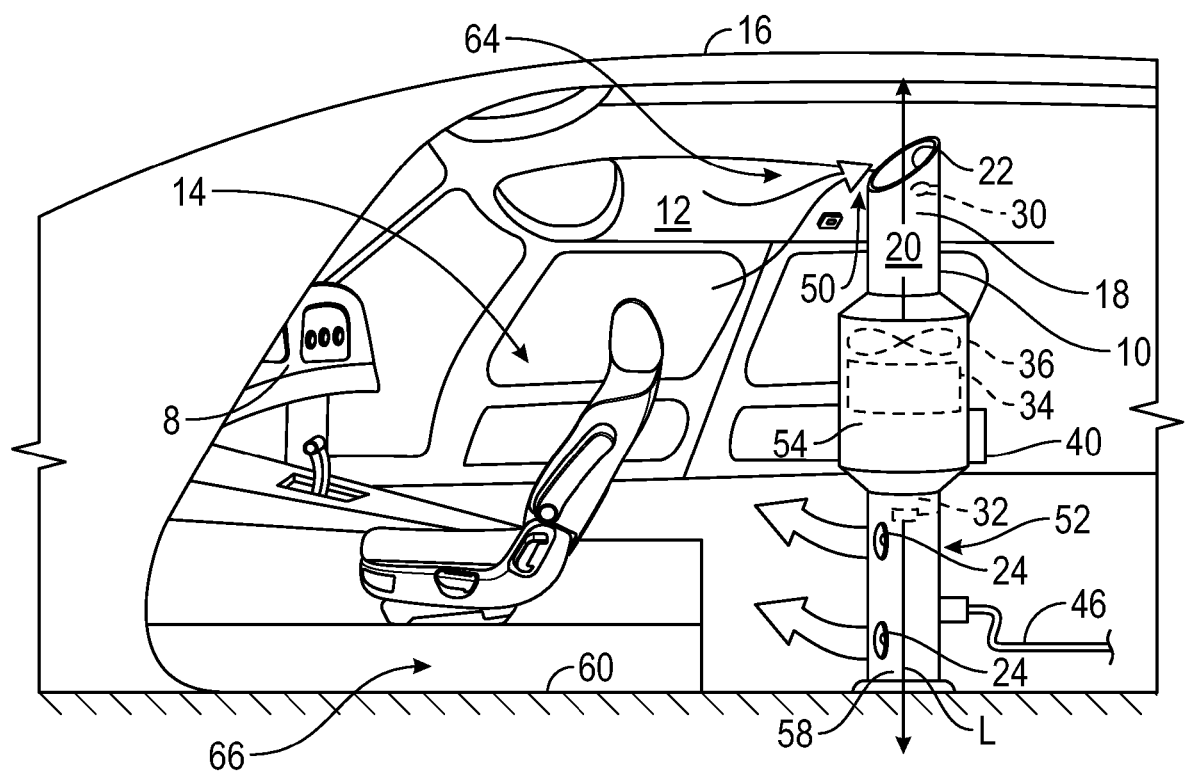
FIG. 1 is a schematic diagram of the disclosed thermal disinfecting tool including a housing, a heater, a fan, and a control module, where the thermal disinfecting tool is located within a flight deck of an aircraft, according to an exemplary embodiment.

Referring to FIG. 1, a thermal disinfecting tool 10 for disinfecting surfaces 8 bounding or located inside a fixed volume of air 12 is illustrated. In the exemplary embodiment as shown in FIG. 1, the thermal disinfecting tool 10 is located within a flight deck 14 of an aircraft 16. The fixed volume of air 12 represents the air located within the flight deck 14 of the aircraft 16 when a door (not shown) to the flight deck 14 is closed. The thermal disinfecting tool 10 includes a housing 20 defining a duct 18, one or more inlets 22, and one or more outlets 24. In the embodiment as shown, the duct 18 extends in a longitudinal direction L between the one or more inlets 22 and the one or more outlet 24 of the housing 20. Air is drawn from the fixed volume of air 12 into the housing 20 through the one or more inlets 22, travels through the duct 18, and exits the housing through the one or more outlets 24. The thermal disinfecting tool 10 also includes one or more inlet sensors 30 configured to monitor a current inlet temperature of the air entering the housing 20, one or more outlet sensors 32 configured to monitor a current outlet temperature exiting the housing 20, a heater 34 configured to generate heat, a fan 36, and a control module 40. The control module 40 is in electronic communication with the one or more inlet sensors 30, the one or more outlet sensors 32, the heater 34, and the fan 36.

Figure 4:
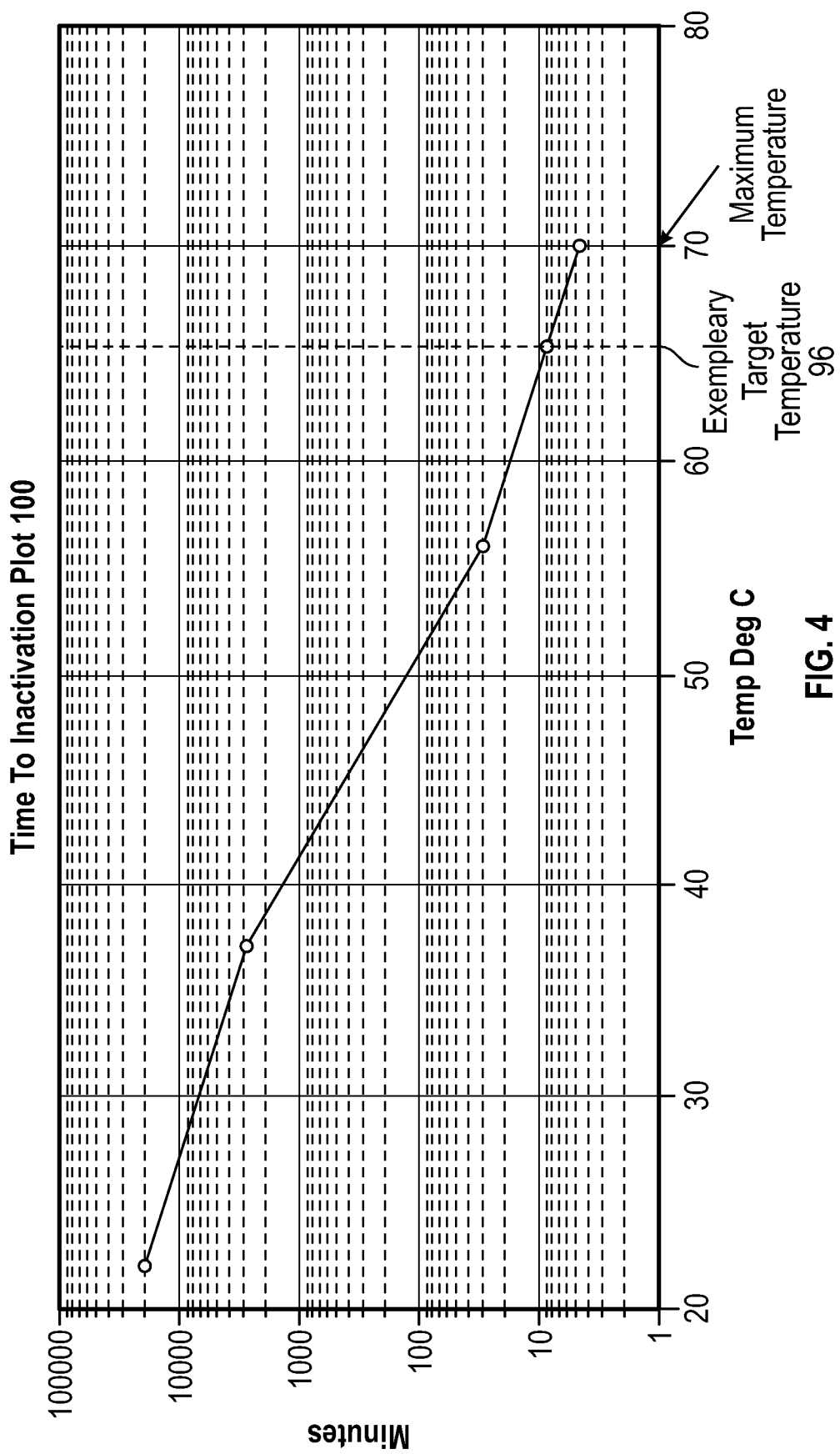
FIG. 4 is a graph illustrating a time to inactivation plot for a specific pathogen, according to an exemplary embodiment.
Figure 5:
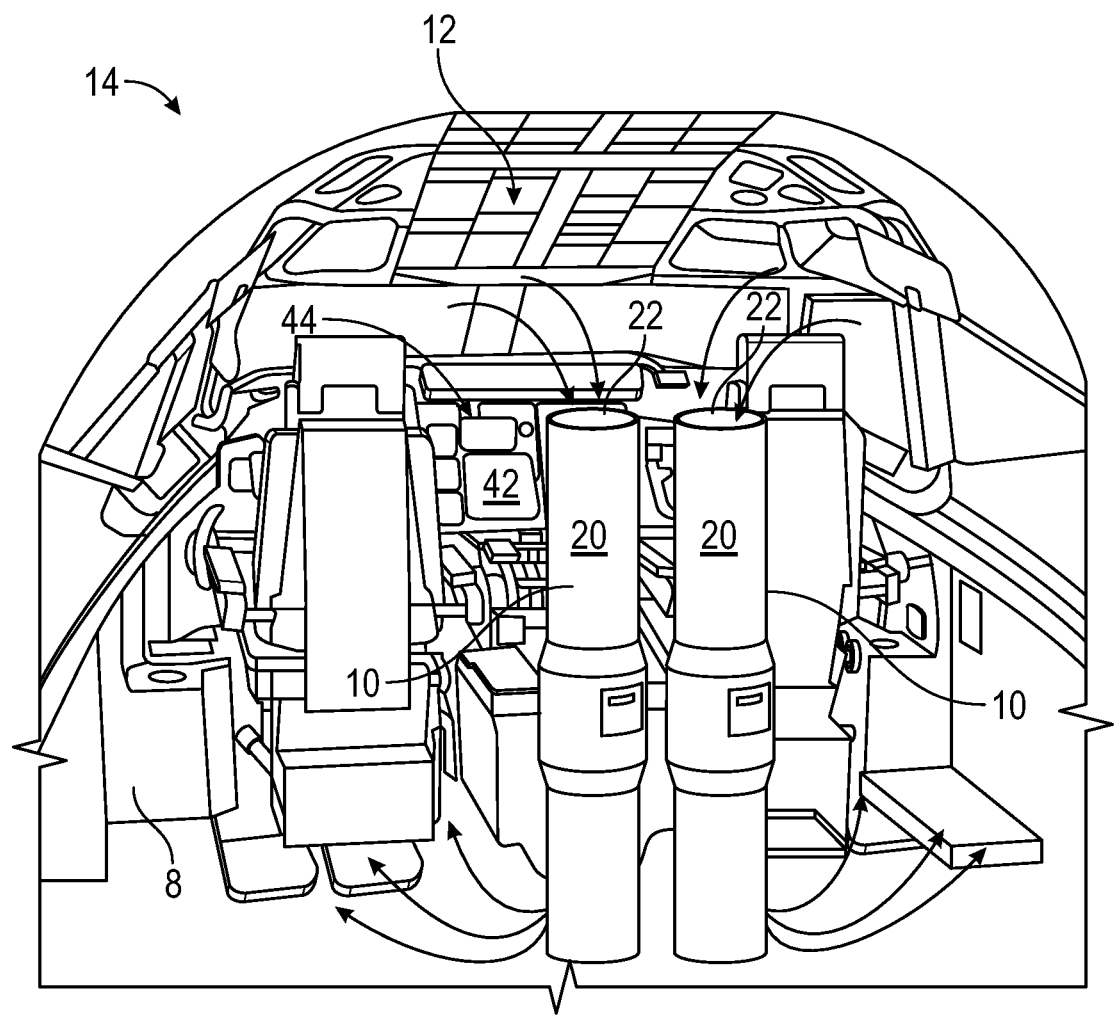
FIG. 5 is an illustration of two thermal disinfecting tools located on the flight deck of the aircraft, according to an exemplary embodiment.

The control module 40 employs feedback to regulate the temperature of the air exiting the housing 20 from the one or more outlets 24. As explained below, the control module 40 calculates an amount of time required to disinfect the surfaces 8 bounding or located inside the fixed volume of air 12. The fixed volume of air 12 represents the air that is located within the flight deck 14 of the aircraft 16 when then door leading to the flight deck 14 has been closed. It is to be appreciated that disinfecting the surfaces 8 bounding or located inside the fixed volume of air 12 in the flight deck 14 deactivates pathogens such as viruses and bacteria that are disposed on the surfaces 42 of the various avionics equipment 44 located in the flight deck 14 (FIG. 4). Although the figures illustrate the thermal disinfection tool 10 employed on the flight deck 14 of the aircraft 16, it is to be appreciated this is merely exemplary in nature. Indeed, the thermal disinfecting tool 10 is not limited to an aircraft and may be used in a variety of other applications as well.

The thermal disinfecting tool 10 is relatively lightweight and compact, and therefore is portable. In other words, the thermal disinfecting tool 10 is sized so that an individual is able to pick up and transport the thermal disinfecting tool 10 from place to place. In the embodiment as shown in FIG. 1, the thermal disinfecting tool 10 includes an electrical cable 46 configured to temporarily connect the thermal disinfecting tool 10 to an external electrical power supply (not shown). For example, in one embodiment, the electrical cable 46 receives electrical power from a ground power unit in a jetway. The electrical cable 46 transmits electrical power from an external source to the one or more inlet sensors 30, the one or more outlet sensors 32, the heater 34, the fan 36, and the control module 40.

In the non-limiting embodiment as shown in FIG. 1, the housing 20 includes a substantially cylindrical profile defining an upper end portion 50, a lower end portion 52, and a side surface 54 connecting the upper end portion 50 to the lower end portion 52. The one or more inlets 22 are located at the upper end portion 50 of the housing 20. The one or more outlets 24 are disposed along the side surface 54, and a base 58 is located at the lower end portion 52 of the housing 20. The base 58 of the housing 20 is seated on a floor 60 of the flight deck 14. Since the one or more inlets 22 are located at the upper end portion 50 of the housing 20, the thermal disinfecting tool 10 draws air from an upper portion 64 of the fixed volume of air 12. Similarly, the one or more outlets 24 are located at the lower end portion 52 of the housing 20. Therefore, air is discharged from the thermal disinfecting tool 10 and back into a lower portion 66 of the flight deck 14. Drawing air from the upper portion 64 of the flight deck 14 and discharging air into the lower portion 66 of the flight deck 14 facilitates air circulation throughout the flight deck 14.

The one or more inlet sensors 30 are configured to detect a current inlet temperature of the air entering the housing 20. It is to be appreciated that the current inlet temperature of the air entering the housing 20 is representative of a current temperature of the fixed volume of air 12 within the flight deck 14. In the embodiment as shown in FIG. 1, the one or more inlet sensors 30 are located directly adjacent to the inlet 22 within the housing 20. However, the one or more inlet sensors 30 may be placed in other locations within the housing 20 upstream of the heater 34 and the fan 36. Similarly, the more or more outlet sensors 32 are configured to monitor an outlet temperature of the air exiting the housing 20. In the non-limiting embodiment as shown in FIG. 1, the one or more outlet sensors 32 are located directly adjacent to the outlets 24. However, the one or more outlet sensors 32 are not limited to the position as shown in FIG. 1 and may be located in other locations within the housing 20, downstream of the heater 34.

Figure 2:
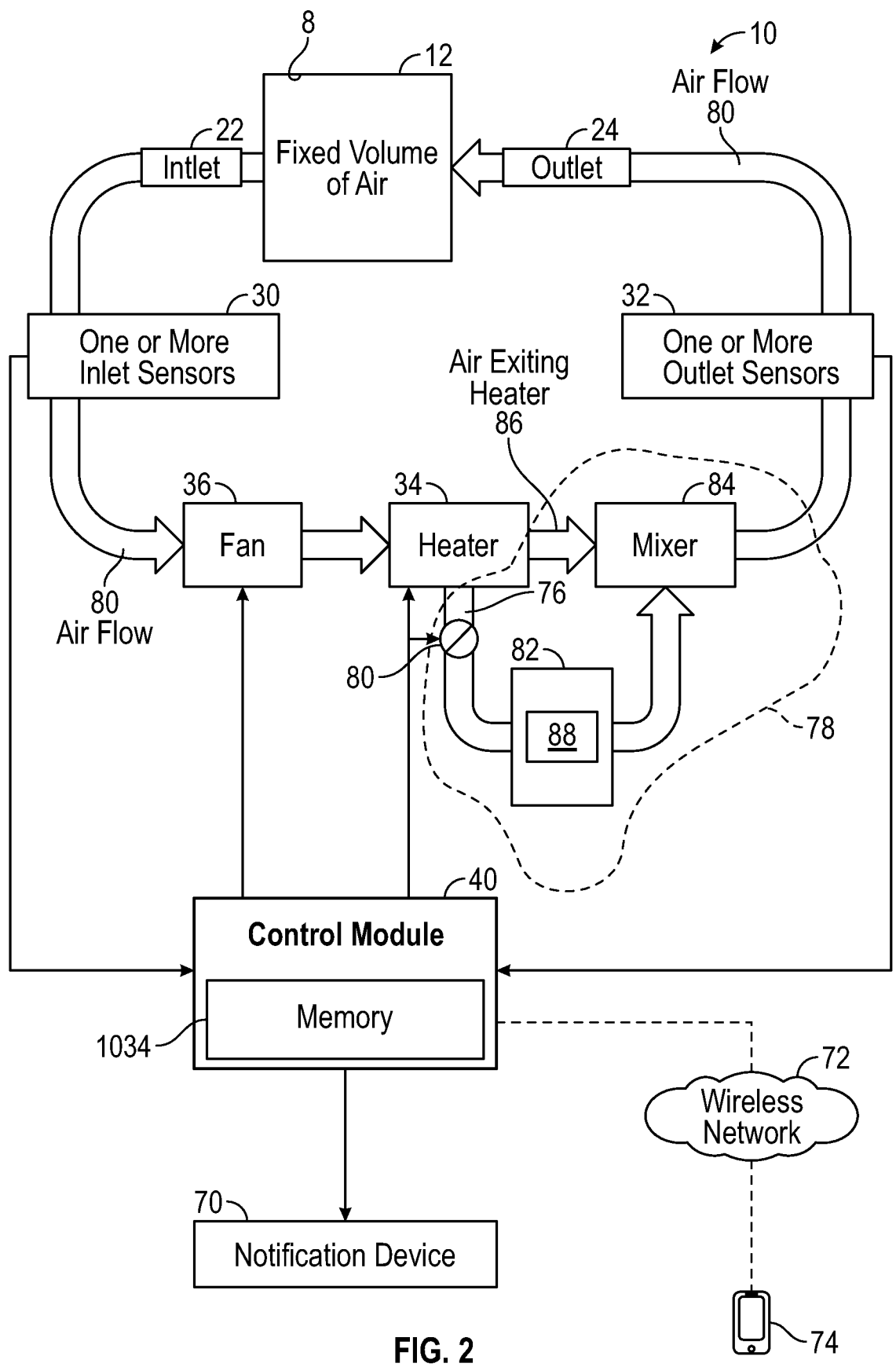
FIG. 2 is a block diagram of the thermal disinfecting tool shown in FIG. 1, according to an exemplary embodiment.

Referring to both FIGS. 1 and 2, the heater 34 is disposed within the housing 20 downstream of the inlet 22 and upstream of the outlet 24 to heat the air before exiting the housing 20 through the one or more outlets 24. The heater 34 is any type of heater configured to heat the air that enters the thermal disinfecting tool 10. For example, in an embodiment, the heater 34 is a resistive heater configured to convert electrical energy into heat. As seen in FIG. 2, the heater 34 is in electronic communication with the control module 40. The control module 40 controls the heater using any number of approaches such as, for example, pulse width modulation (PWM) or variable voltage control.

Continuing to refer to FIGS. 1 and 2, the fan 36 is in electronic communication with the control module 40. The fan 36 is disposed within the housing 20 upstream of the heater 34 and is configured to generate airflow when turned on. The volume of air 12 entering the inlet 22 of the housing 20 is driven in a direction towards the heater 34 by the fan 36. The control module 40 is configured to control the speed of the fan 36 using any number of approaches such as, for example, PWM or variable voltage control.

Referring specifically to FIG. 2, in one embodiment the thermal disinfection tool 10 includes a notification device 70 in electronic communication with the control module 40. The control module 40 instructs the notification device 70 is configured to generate one or more notifications indicating the thermal disinfecting tool 10 has finished disinfecting the surfaces 8 bounding or located inside the fixed volume of air 12. For example, in one embodiment, the notification device is an alarm that emits an audible tone. However, in an alternative embodiment, the control module 40 generates one or more messages that are sent over a wireless network 72 to a personal electronic device 74, and the personal electronic device 74 generates one or more notifications indicating that the thermal disinfecting tool 10 has finished disinfecting the surfaces 8 bounding or located inside the fixed volume of air 12. The personal electronic device 74 may be, for example, an individual's smartphone or laptop computer.

Referring to both FIGS. 1 and 2, in one exemplary embodiment the thermal disinfecting tool 10 is placed in the flight deck 14 of the aircraft 16. An individual may then activate the thermal disinfecting tool 10, exit the flight deck 14, and close a door leading to the flight deck 14. The individual receives one or more notifications generated by the thermal disinfecting tool 10 once the surfaces 8 bounding or located inside the fixed volume of air 12 in the flight deck 14 has been disinfected. Thus, the disinfection process requires limited human interaction.

Referring specifically to FIG. 2, in one non-limiting embodiment, the thermal disinfecting tool 10 includes a humidifier 78 that is configured to increase the humidity of the air exiting the thermal disinfecting tool 10. Specifically, the humidifier 78 includes an optional airflow valve 80, a sump 82, and a mixer 84. The airflow valve 80 is configured to divert a portion 76 of the air exiting the heater 86 to the humidifier 78. Referring to both FIGS. 1 and 2, the sump 82 is disposed at the lower end portion 52 of the housing 20 of the thermal disinfecting tool 10. In one embodiment, the sump 82 includes an absorptive pad 88 containing water, and the portion 76 of air exiting the heater 86 blows across the absorptive pad 88. Thus, the portion 76 of air exiting the heater 86 becomes saturated with water. The portion 76 of air exiting the heater 86 is then combined with the remaining air exiting the heater 86 at the mixer 84. In an embodiment, if the airflow valve 80 is omitted, then the portion 76 of the air flowing through the humidifier 78 is instead fixed at a rate previously determined to be acceptable for most or all circumstances.

The airflow valve 80 is in electronic communication with the control module 40. In an embodiment, the control module 40 sets the airflow valve 80 to a predetermined position. Thus, the portion 76 diverted from the air exiting the heater 86 is fixed. Alternatively, in another embodiment, the control module 40 actively adjusts a position of the airflow valve 80 to either increase or decrease a relative humidity of the air exiting the one or more inlets 22 of the thermal disinfecting tool 10. It is to be appreciated that the relative humidity of the air exiting the thermal disinfecting tool 10 is determined based on a specific environment of the fixed volume of air 12 and the specific pathogen that the thermal disinfecting tool 10 is deactivating from the surfaces 8 bounding or inside the fixed volume of air 12. For example, the relative humidity may be set at a percentage that is recommended for aircraft avionics. Furthermore, as another example, certain types of viruses are destroyed more easily when the relative humidity is increased. Therefore, in an embodiment, the control module 40 adjusts the relative humidity of the air exiting the thermal disinfecting tool 10 based on the specific application as well as the specific type of pathogen that is being destroyed or inactivated.

Figure 3:
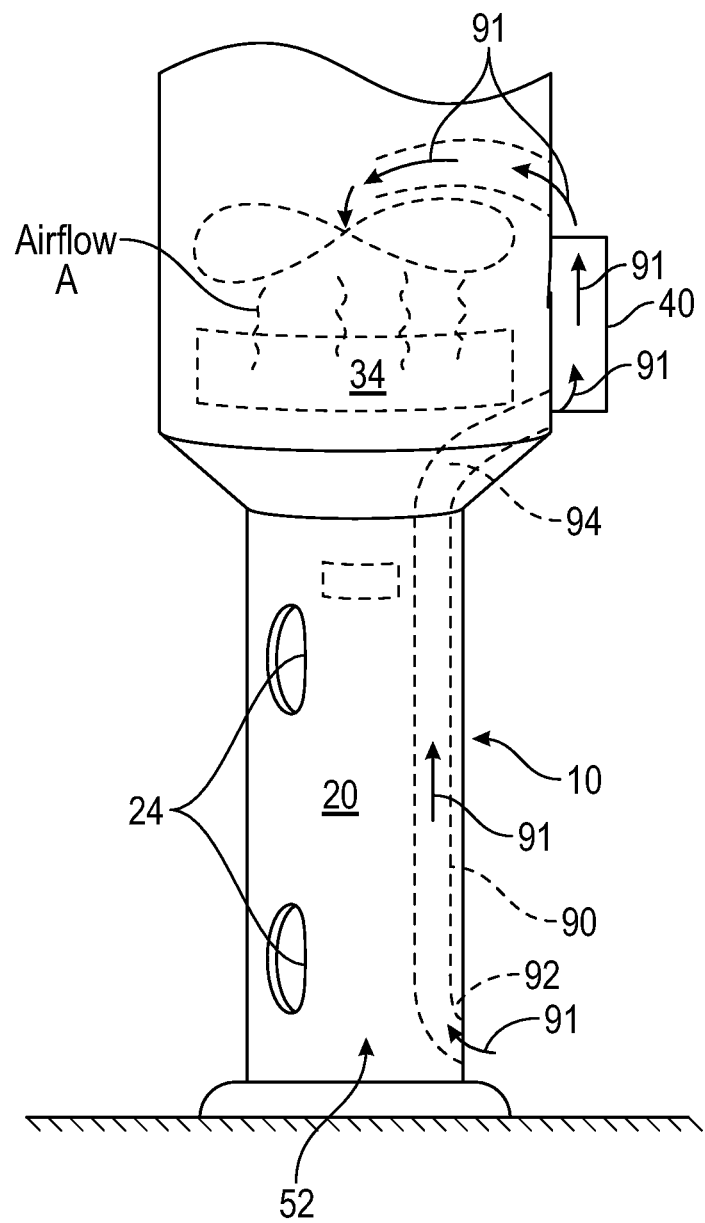
FIG. 3 is an enlarged view of a lower end portion of the housing of the thermal disinfectant tool, according to an exemplary embodiment.

Referring now to FIG. 3, the housing 20 includes a secondary duct 90 defining a secondary inlet 92 and a secondary outlet 94 configured to provide a stream of cooling air that is directed through the control module 40. The secondary duct 90 is located at the lower end portion 52 of the housing 20 and the secondary outlet 94 terminates inside the housing 20, directly adjacent to the fan 36. Cooling air 91 enters the secondary inlet 92, passes through the control module 40, and exits the secondary duct 90 through the secondary outlet 94 and into the airstream A generated by the fan 36.

Referring to FIGS. 2 and 4, the control module 40 includes a memory 1034. The memory 1034 of the control module 40 stores a time to inactivation plot 100 for a specific pathogen, which is illustrated in FIG. 4. As seen in FIG. 4, the time to inactivation plot 100 indicates a deactivation time for the specific pathogen over a range of temperatures. For example, in the embodiment as shown in FIG. 4, the range of temperatures range from 20° C. to 80° C., however, it is to be appreciated that the range of temperatures may vary based on the specific pathogen. The time to inactivation plot 100 includes an x-axis that indicates temperature and a y-axis having a logarithmic scale indicating time. For example, at 50° C. the specific pathogen would be deactivated in about 50 minutes. In the embodiment as shown in FIG. 4, the inactivation plot 100 is for a specific coronavirus. In one embodiment, the memory 1034 of the control module 40 stores a plurality of time to inactivation plots 100 for a number of different pathogens as well. Therefore, the thermal disinfecting tool 10 is configured to deactivate a number of different viruses, bacteria, and fungi.

Continuing to refer to FIGS. 2 and 4, the control module 40 calculates a disinfection rate for the surfaces 8 bounding or inside the fixed volume of air 12 based on the time to inactivation plot 100 stored in the memory 1034 for each current inlet temperature detected by the one or more inlet sensors 30 up to the target temperature. The disinfection rate indicates a period of time required to deactivate the specific pathogen within the surfaces 8 bounding or inside the fixed volume of air 12 at the current inlet temperature until a target temperature 96 is reached. The specific pathogen is deactivated within a threshold period of time at the target temperature 96. Thus, it is to be appreciated that the control module 40 considers the previous temperatures detected by the one or more inlet sensors 30 into account when calculating the disinfection rate for the surfaces 8 bounding or inside the fixed volume of air 12.

For example, in the non-limiting embodiment as shown in FIG. 4, the exempleary target temperature 96 is about 65° C. and the threshold period of time is about ten minutes. In this example, the control module 40 considers the disinfection that occurred at the various temperatures located along the time to inactivation plot 100 prior to the target temperatures 96. In the present example, this means that the actual time to disinfection is less than ten minutes since the control module 40 considered the disinfection at the current inlet temperatures up to the target temperature 96 when calculating the time to disinfection. In other words, the period of time required to deactivate the specific pathogen on the surfaces 8 bounding or inside the fixed volume of air 12 is less than the threshold period of time at the target temperature 96.

Referring to FIGS. 1 and 2, the control module 40 also monitors the one or more outlet sensors 32 for the outlet temperature of the air to ensure that the air exiting the one or more outlets 24 does not exceed a maximum temperature 98. The maximum temperature 98 is based on the specific environment that the fixed volume of air 12 is located within. For example, in the embodiment as shown in FIGS. 1 and 2, the maximum temperature 98 is about 70° C., which is a maximum operating temperature of aircraft avionics. In other words, the thermal disinfecting tool 10 limits the temperature of the air exiting the one or more outlets 24 based on the environment that the fixed volume of air 12 is located within.

In an embodiment, the control module 40 compares the inlet temperature of the air with the maximum temperature 98, and in response to determining the outlet temperature is less than the maximum temperature 98, the control module 40 continues to instruct the heater 34 to generate heat. However, in response to determining the outlet temperature is equal to or greater than the maximum temperature 98, the control module 40 instruct the heater to either reduce or cease generating heat.

Figure 6A:
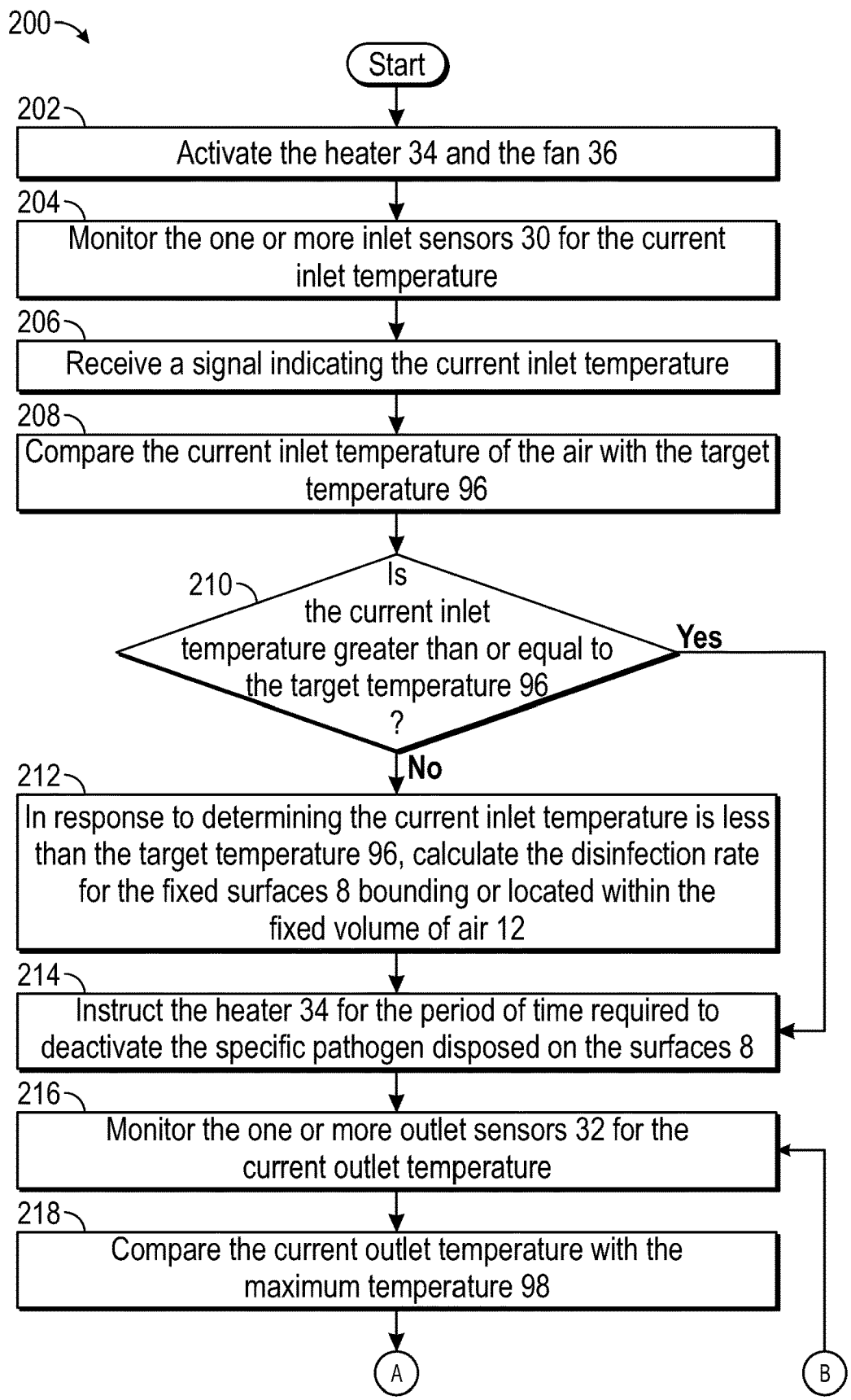
FIGS. 6A-6B illustrate an exemplary process flow diagram illustrating a method for disinfecting surfaces bounding or inside a fixed volume of air using the disclosed thermal disinfecting tool, according to an exemplary embodiment.
Figure 6B:
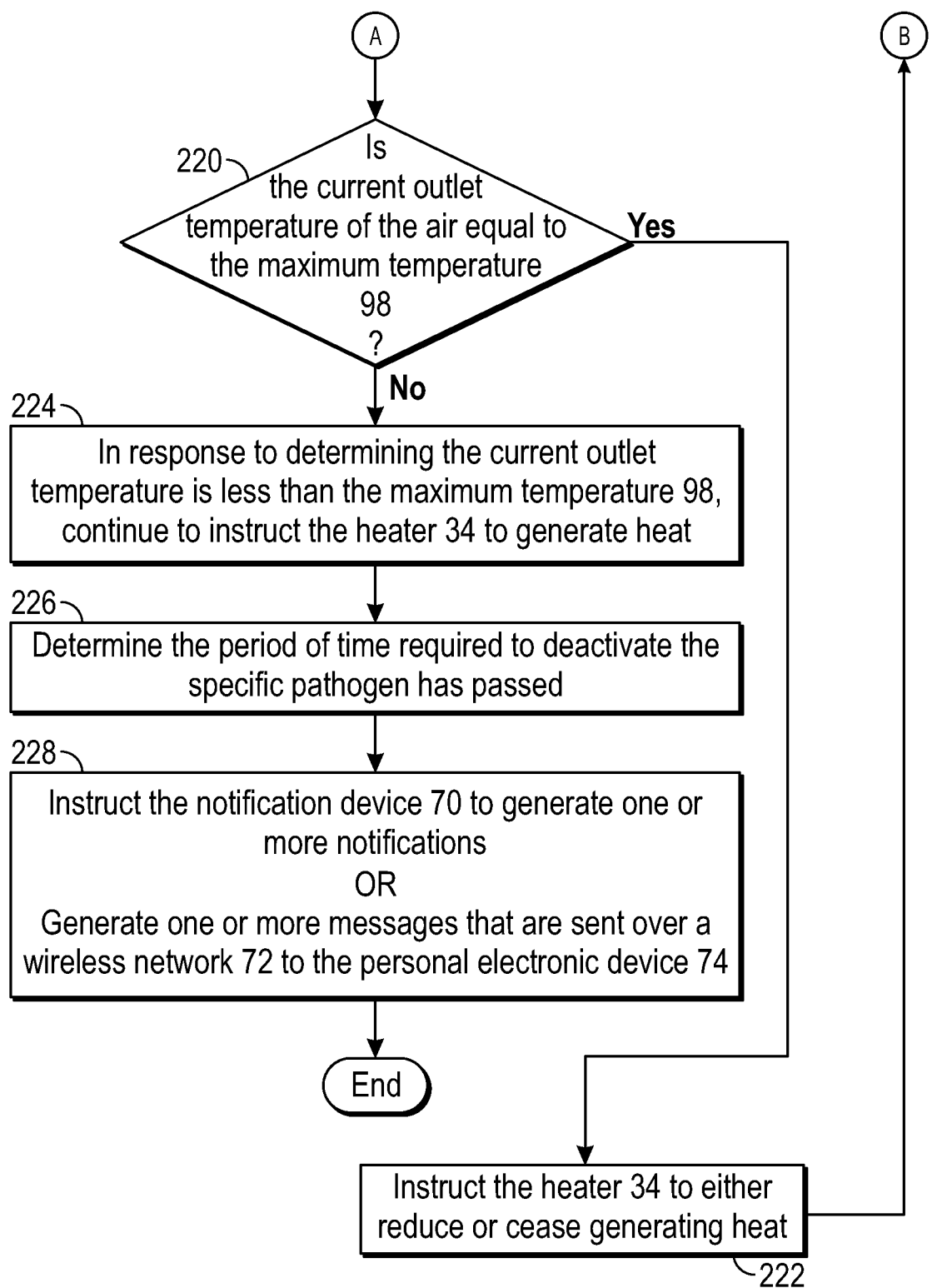

FIGS. 6A-6B illustrate a process flow diagram illustrating an exemplary method 200 for disinfecting the surfaces 8 bounding or inside the fixed volume of air 12 by the thermal disinfecting tool 10. Referring to FIGS. 1, 2, 4, and 6A, the method 200 begins at block 202. In block 202, the control module 40 activates the heater 34 and the fan 36. The method 200 may then proceed to block 204.

In block 204, the control module 40 monitors the one or more inlet sensors 30 for the current inlet temperature of the air entering the one or more inlets 22 of the housing 20. The method 200 may then proceed to block 206.

In block 206, the control module 40 receives a signal indicating the current inlet temperature of air entering the one or more inlets 22 of the housing 20. The method 200 may then proceed to block 208.

In block 208, the control module 40 compares the current inlet temperature of the air with the target temperature 96 located on the time to inactivation plot 100 stored in the memory 1034. The method 200 may then proceed to block 210.

In decision block 210, if the current inlet temperature is greater than or equal to the target temperature, then the method 200 proceeds to block 214. However, if the current inlet temperature is less than the target temperature, then the method 200 proceeds to block 212.

In block 212, in response to determining the current inlet temperature is less than the target temperature 96, the control module 40 calculates the disinfection rate for the surfaces 8 bounding or inside the fixed volume of air 12 based on the time to inactivation plot 100 for each current inlet temperature up to the target temperature 96. As mentioned above, the disinfection rate indicates the period of time required to deactivate the specific pathogen disposed on the surfaces 8 bounding or inside the fixed volume of air 12 at the current inlet temperature until the target temperature 96 is reached. It is to be appreciated that in one embodiment, the control module 40 determines the surfaces 8 within or bounding the fixed volume of air 12 have been disinfected without the current inlet temperature ever achieving the target temperature 96. The method 200 may then proceed to block 214.

In block 214, the control module 40 instructs the heater 34 to generate heat for the period of time required to deactivate the specific pathogen. The method 200 may then proceed to block 216.

In block 216, the control module 40 monitors the one or more outlet sensors 32 for the current outlet temperature. The method 200 may then proceed to block 218.

Referring to FIG. 6B, in block 218 the control module 40 compares the current outlet temperature of the air with the maximum temperature 98. The method 200 may then proceed to decision block 220.

In decision block 220, if the current outlet temperature of the air is equal to the maximum temperature 98, then the method 200 proceeds to block 222. In block 222, the control module 40 instructs the heater 34 to either reduce or cease generating heat. The method may then proceed back to block 216. However, if the control module 40 determines the current outlet temperature is less than the maximum temperature 98, then the method 200 proceeds to block 224.

In block 224, in response to determining the current outlet temperature is less than the maximum temperature 98, the control module 40 continues to instruct the heater 34 to generate heat. The method 200 may then proceed to block 226.

In block 226, the control module 40 determines that the period of time required to deactivate the specific pathogen disposed on the surfaces 8 bounding or located inside the fixed volume of air at the current inlet temperature has passed, and the surfaces 8 bounding or inside the fixed volume of air 12 are disinfected. The method 200 may then proceed to block 228.

In block 228, in response to determining the period of time required to deactivate the specific pathogen on the surfaces bounding or inside the fixed volume of air at the current inlet temperature has passed, and the surfaces bounding or inside the fixed volume of air 12 are disinfected, the control module 40 instructs the notification device 70 to generate one or more notifications indicating the thermal disinfecting tool 10 has finished disinfecting the surfaces bounding or inside the fixed volume of air 12. In an alternative embodiment, the control module 40 generates one or more messages that are sent over a wireless network 72 to the personal electronic device 74. In response to receiving the one or more messages, the personal electronic device 74 generates one or more notifications indicating that the thermal disinfecting tool 10 has finished disinfecting the surfaces bounding or inside the fixed volume of air 12. The method 200 may then terminate.

Referring generally to the figures, the disclosed thermal disinfecting tool provides various technical effects and benefits. Specifically, the thermal disinfecting tool provides a cost-effective and relatively simple for approach for disinfecting the surfaces bounding or located within a volume of air. The disclosed thermal disinfection tool requires limited human involvement and does not require any specialized training or knowledge to operate, unlike some other tools that are currently available for disinfection. Furthermore, the disclosed thermal disinfection tool does not require line-of-sight exposure of the contaminants, unlike tools that employ ultraviolet light to deactivate pathogens.

Figure 7:
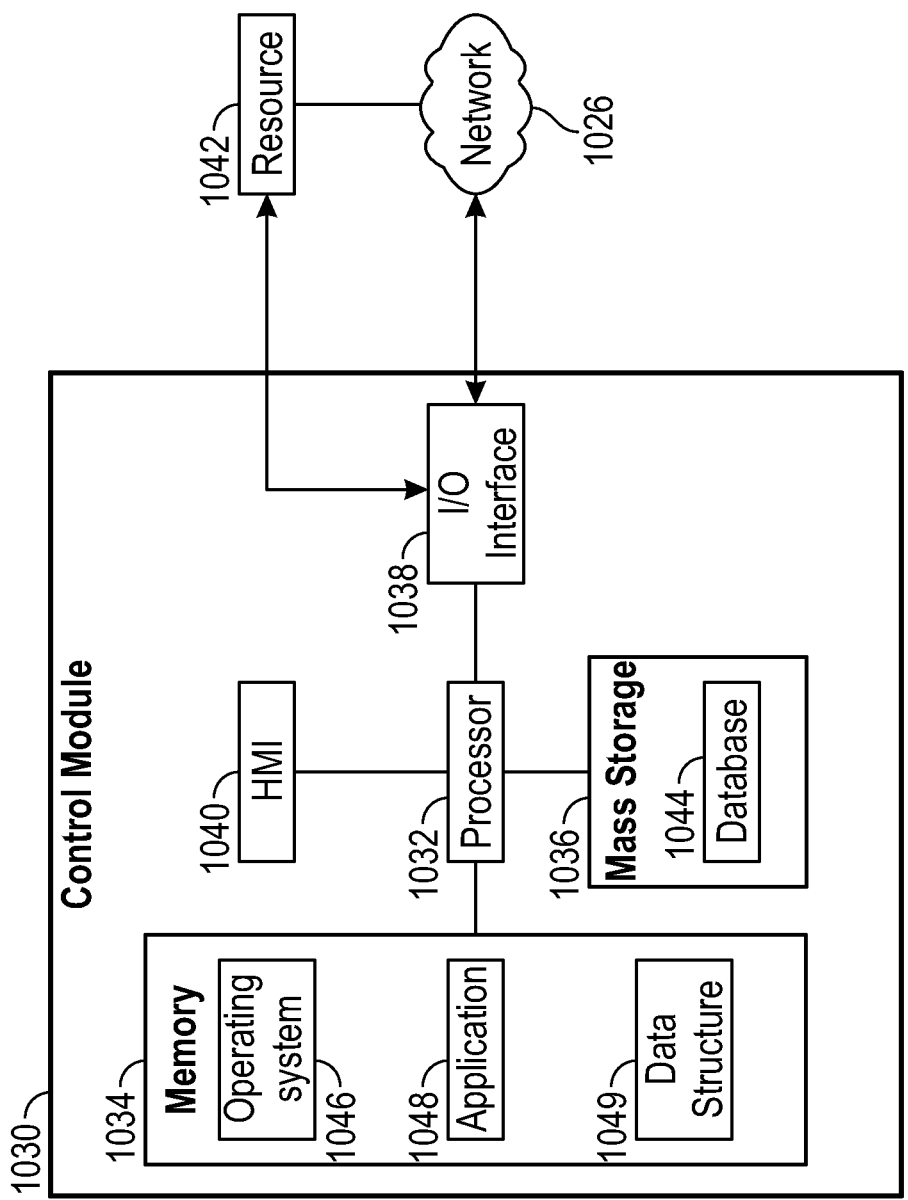
FIG. 7 illustrates the control module for the disclosed system, according to an exemplary embodiment.

Referring to FIG. 7, the control module 40 is implemented on one or more computer devices or systems, such as exemplary computer system 1030. The computer system 1030 includes a processor 1032, a memory 1034, a mass storage memory device 1036, an input/output (I/O) interface 1038, and a Human Machine Interface (HMI) 1040. The computer system 1030 is operatively coupled to one or more external resources 1042 via the network 1026 or I/O interface 1038. External resources may include, but are not limited to, servers, databases, mass storage devices, peripheral devices, cloud-based network services, or any other suitable computer resource that may be used by the computer system 1030.

The processor 1032 includes one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 1034. Memory 1034 includes a single memory device or a plurality of memory devices including, but not limited to, read-only memory (ROM), random access memory (RAM), volatile memory, non-volatile memory, static random-access memory (SRAM), dynamic random-access memory (DRAM), flash memory, cache memory, or any other device capable of storing information. The mass storage memory device 1036 includes data storage devices such as a hard drive, optical drive, tape drive, volatile or non-volatile solid-state device, or any other device capable of storing information.

The processor 1032 operates under the control of an operating system 1046 that resides in memory 1034. The operating system 1046 manages computer resources so that computer program code embodied as one or more computer software applications, such as an application 1048 residing in memory 1034, may have instructions executed by the processor 1032. In an alternative example, the processor 1032 may execute the application 1048 directly, in which case the operating system 1046 may be omitted. One or more data structures 1049 also reside in memory 1034, and may be used by the processor 1032, operating system 1046, or application 1048 to store or manipulate data.

The I/O interface 1038 provides a machine interface that operatively couples the processor 1032 to other devices and systems, such as the network 1026 or external resource 1042. The application 1048 thereby works cooperatively with the network 1026 or external resource 1042 by communicating via the I/O interface 1038 to provide the various features, functions, applications, processes, or modules comprising examples of the disclosure. The application 1048 also includes program code that is executed by one or more external resources 1042, or otherwise rely on functions or signals provided by other system or network components external to the computer system 1030. Indeed, given the nearly endless hardware and software configurations possible, persons having ordinary skill in the art will understand that examples of the disclosure may include applications that are located externally to the computer system 1030, distributed among multiple computers or other external resources 1042, or provided by computing resources (hardware and software) that are provided as a service over the network 1026, such as a cloud computing service.

The HMI 1040 is operatively coupled to the processor 1032 of computer system 1030 in a known manner to allow a user to interact directly with the computer system 1030. The HMI 1040 may include video or alphanumeric displays, a touch screen, a speaker, and any other suitable audio and visual indicators capable of providing data to the user. The HMI 1040 also includes input devices and controls such as an alphanumeric keyboard, a pointing device, keypads, pushbuttons, control knobs, microphones, etc., capable of accepting commands or input from the user and transmitting the entered input to the processor 1032.

A database 1044 may reside on the mass storage memory device 1036 and may be used to collect and organize data used by the various systems and modules described herein. The database 1044 may include data and supporting data structures that store and organize the data. In particular, the database 1044 may be arranged with any database organization or structure including, but not limited to, a relational database, a hierarchical database, a network database, or combinations thereof. A database management system in the form of a computer software application executing as instructions on the processor 1032 may be used to access the information or data stored in records of the database 1044 in response to a query, where a query may be dynamically determined and executed by the operating system 1046, other applications 1048, or one or more modules.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A thermal disinfecting tool for disinfecting surfaces bounding or located inside a fixed volume of air, the thermal disinfecting tool comprising:
   a housing defining one or more inlets and one or more outlets, wherein air enters the housing through the one or more inlets and exits the housing through the one or more outlets;
   a heater configured to generate heat, wherein the heater is disposed within the housing downstream of the one or more inlets and upstream of the one or more outlets;
   one or more processors in electronic communication with the heater; and
   a memory coupled to the one or more processors, the memory storing a time to inactivation plot for a specific pathogen that indicates a deactivation time for the specific pathogen over a range of temperatures, and wherein the memory stores data into one or more databases and program code that, when executed by the one or more processors, causes the thermal disinfecting tool to:

receive a signal indicating a current inlet temperature of air entering the one or more inlets of the housing;

compare the current inlet temperature of the air with a target temperature located on the time to inactivation plot stored in the memory;

in response to determining the current inlet temperature is less than the target temperature, calculate a disinfection rate for the surfaces bounding or located within the fixed volume of air based on the time to inactivation plot for each current inlet temperature up to the target temperature, wherein the disinfection rate indicates a period of time required to deactivate the specific pathogen disposed on the surfaces bounding or located within the fixed volume of air at the current inlet temperature until the target temperature is reached; and instruct the heater to generate heat for the period of time required to deactivate the specific pathogen.

2. The thermal disinfecting tool of claim 1, further comprising one or more outlet sensors configured to monitor a current outlet temperature of the air exiting the one or more outlets of the housing.

3. The thermal disinfecting tool of claim 2, wherein the one or more processors execute instruction to:

monitor the one or more outlet sensors for the current outlet temperature;

compare the current outlet temperature of the air with a maximum temperature; and in response to determining the current outlet temperature is less than the maximum temperature, continue to instruct the heater to generate heat.

4. The thermal disinfecting tool of claim 3, wherein the one or more processors execute instruction to:

in response to determining the current outlet temperature is equal to or greater than the maximum temperature, instruct the heater to either reduce or cease generating heat.

5. The thermal disinfecting tool of claim 3, wherein the maximum temperature is a maximum operating temperature of aircraft avionics.

6. The thermal disinfecting tool of claim 1, further comprising one or more inlet sensors in electronic communication with the one or more processors, wherein the one or more inlet sensors are configured to monitor the current inlet temperature of the air entering the one or more inlets of the housing.

7. The thermal disinfecting tool of claim 1, wherein the specific pathogen is deactivated within a threshold period of time at the target temperature.

8. The thermal disinfecting tool of claim 7, wherein the period of time required to deactivate the specific pathogen disposed on the surfaces bounding or located within the fixed volume of air is less than the threshold period of time.

9. The thermal disinfecting tool of claim 1, further comprising a humidifier configured to increase the humidity of the air exiting the thermal disinfecting tool, wherein the humidifier includes an airflow valve, a sump, and a mixer.

10. The thermal disinfecting tool of claim 9, wherein the airflow valve is configured to divert a portion of the air exiting the heater to the sump.

11. The thermal disinfecting tool of claim 10, wherein the airflow valve is in electronic communication with the one or more processors, and wherein the one or more processors execute instruction to:

actively adjust a position of the airflow valve to either increase or decrease a relative humidity of the air exiting the one or more inlets of the thermal disinfecting tool based on a specific environment of the fixed volume of air and the specific pathogen.

12. The thermal disinfecting tool of claim 1, further comprising a fan in electronic communication with the one or more processors, wherein the fan is located within the housing upstream of the heater.

13. The thermal disinfecting tool of claim 12, wherein the housing includes a secondary duct defining a secondary inlet and a secondary outlet, wherein cooling air enters the secondary inlet, passes through the one or more processors, and exits the secondary duct through the secondary outlet and into an airstream generated by the fan.

14. The thermal disinfecting tool of claim 1, further comprising a notification device in electronic communication with the one or more processors, wherein the one or more processors execute instructions to:

determine the period of time required to deactivate the specific pathogen disposed on surfaces bounding or located within the fixed volume of air at the current inlet temperature has passed; and in response to determining the period of time required to deactivate the specific pathogen disposed on the surfaces bounding or located within the fixed volume of air has passed, instruct the notification device to generate one or more notifications indicating the thermal disinfecting tool has finished disinfecting the surfaces bounding or located within the fixed volume of air.

15. The thermal disinfecting tool of claim 1, wherein the one or more processors execute instructions to:

determine the period of time required to deactivate the specific pathogen disposed on the surfaces bounding or located within the fixed volume of air at the current inlet temperature has passed; and in response to determining the period of time required to deactivate the specific pathogen disposed on the surfaces bounding or located within the fixed volume of air has passed, generate one or more messages that are sent over a wireless network to a personal electronic device.

16. A method for disinfecting surfaces bounding or located within a fixed volume of air by a thermal disinfecting tool, the method comprising:

activating, by a control module, a heater, wherein a housing defines one or more inlets and one or more outlets where air enters the housing through the one or more inlets and exits the housing through one or more outlets, and wherein the heater is disposed within the housing downstream of the one or more inlets and upstream of the one or more outlets of the thermal disinfecting tool;

receiving, by a control module, a signal indicating a current inlet temperature of air entering the one or more inlets of the housing;

comparing, by the control module, the current inlet temperature of the air with a target temperature located on a time to inactivation plot stored in a memory of the control module, wherein the time to inactivation plot is for a specific pathogen and indicates a deactivation time for the specific pathogen over a range of temperatures;

in response to determining the current inlet temperature is less than the target temperature, calculating a disinfection rate for the surfaces bounding or located within the fixed volume of air based on the time to inactivation plot for each current inlet temperature up to the target temperature, wherein the disinfection rate indicates a period of time required to deactivate the specific pathogen disposed on the surfaces bounding or located within the fixed volume of air at the current inlet temperature until the target temperature is reached; and instructing the heater to generate heat for the period of time required to deactivate the specific pathogen.

17. The method of claim 16, further comprising:

receiving, by the control module, a signal indicating a current outlet temperature of air exiting the housing;

comparing the current outlet temperature of the air with a maximum temperature; and in response to determining the current outlet temperature is less than the maximum temperature, continuing to instruct the heater to generate heat.

18. The method of claim 17, further comprising:

in response to determining the current outlet temperature is equal to or greater than the maximum temperature, instructing the heater to either reduce or cease generating heat.

19. The method of claim 16, further comprising:

determining the period of time required to deactivate the specific pathogen disposed on the surfaces bounding or located within the fixed volume of air at the current inlet temperature has passed; and in response to determining the period of time required to deactivate the specific pathogen disposed on the surfaces bounding or located within the fixed volume of air has passed, instructing a notification device to generate one or more notifications indicating the thermal disinfecting tool has finished disinfecting the surfaces bounding or located within the fixed volume of air.

20. The method of claim 16, further comprising:

determining the period of time required to deactivate the specific pathogen disposed on the surfaces bounding or located within the fixed volume of air at the current inlet temperature has passed; and in response to determining the period of time required to deactivate the specific pathogen disposed on the surfaces bounding or located within the fixed volume of air has passed, generating one or more messages that are sent over a wireless network to a personal electronic device.

* * * * *